(12) United States Patent
Buerger et al.

(10) Patent No.: US 7,312,216 B2
(45) Date of Patent: *Dec. 25, 2007

(54) N-PHENYL-2-PYRIMIDINE-AMINE DERIVATIVES

(75) Inventors: Hans M Buerger, Allschwil (CH); Giorgio Caravatti, Bottmingen (CH); Uerg Zimmermann, Binningen (CH); Paul W Manley, Arlesheim (CH); Werner Breitenstein, Basel (CH); Margaret A Cudd, Muenchenstein (CH)

(73) Assignee: Novartis AG, Basel (CH)

(*) Notice: Subject to any disclaimer, the term of this patent is extended or adjusted under 35 U.S.C. 154(b) by 0 days.

This patent is subject to a terminal disclaimer.

(21) Appl. No.: 11/448,649

(22) Filed: Jun. 7, 2006

(65) Prior Publication Data

US 2006/0223818 A1    Oct. 5, 2006

Related U.S. Application Data

(62) Division of application No. 10/363,841, filed as application No. PCT/EP01/10503 on Sep. 11, 2001, now Pat. No. 7,081,532.

(30) Foreign Application Priority Data

Sep. 13, 2000    (GB) .................................. 0022438.6

(51) Int. Cl.
A61K 31/506    (2006.01)
C07D 401/04    (2006.01)

(52) U.S. Cl. .............................. 514/235.8; 514/252.18; 514/275; 544/122; 544/295; 544/330; 544/331

(58) Field of Classification Search .................. 544/122, 544/295, 330, 331; 514/235.8, 275, 252.18
See application file for complete search history.

(56) References Cited

U.S. PATENT DOCUMENTS 5,521,184 A    5/1996    Zimmermann 7,081,532 B2 *    7/2006    Buerger et al. ............. 544/295

FOREIGN PATENT DOCUMENTS

EP    0 564 409    10/1993
WO    WO 00/78731    12/2000

OTHER PUBLICATIONS

Zimmerman et al., "Phenylamino-Pyrimidine (PAP)—Derivatives: A New Class of Potent and Highly Selective PDGF-Receptor Autophosphorylation Inhibitors", *Bioorg. Med. Chem. Lett.*, vol. 6, No. 11, pp. 1221-1226 (1996).
Simone, Oncology: INtroduction, Cecil Textbook of Medicine, 20th Edition, vol. 1, pp. 1004-1010 (1996).
Traxler, Protein tyrosine kinase inhibitors in cancer treatment, Exp. Opin. Ther. Patents, 7(6):571-588, (1997).
Tucker et al., Optimizing drug development: Strategies to asess drug metabolism/transporter interaction potential—toward a consensus. Clinical Pharmacology Therapeutics, vol. 70(3), pp. 103-114 (Aug. 2001).

* cited by examiner

*Primary Examiner*—Deepak Rao
(74) *Attorney, Agent, or Firm*—Oona A. Manzari

(57) ABSTRACT

The invention relates to N-phenyl-2-pyrimidine-amine derivatives of formula I

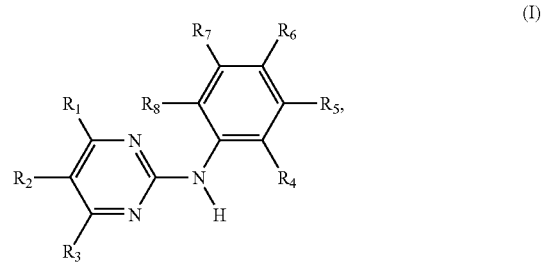

wherein the substituents are defined as indicated in the description, to processes for the preparation thereof, to medicaments comprising those compounds, and to the use thereof in the preparation of pharmaceutical compositions for the therapeutic treatment of warm-blooded animals, including humans.

2 Claims, No Drawings

N-PHENYL-2-PYRIMIDINE-AMINE DERIVATIVES

This application is a divisional of U.S. patent application Ser. No. 10/363 841, filed Mar. 10, 2003 now U.S. Pat. No. 7,081,532, which is a 371 of International Application No. PCT/EP01/10503, filed Sep. 11, 2001.

The invention relates to N-phenyl-2-pyrimidine-amine derivatives, to processes for the preparation thereof, to medicaments comprising those compounds, and to the use thereof in the preparation of pharmaceutical compositions for the therapeutic treatment of warm-blooded animals, including humans.

The invention relates to N-phenyl-2-pyrimidine-amine derivatives of formula I

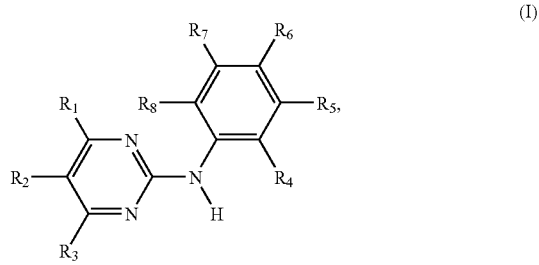

wherein $R_1$ is pyrazinyl; 1-methyl-1H-pyrrolyl; amino- or amino-lower alkyl-substituted phenyl, wherein the amino group in each case is free, alkylated or acylated; 1H-indolyl or 1H-imidazolyl bonded at a five-membered ring carbon atom; or unsubstituted or lower alkyl-substituted pyridyl bonded at a ring carbon atom and unsubstituted or substituted at the nitrogen atom by oxygen, $R_2$ and $R_3$ are each independently of the other hydrogen or lower alkyl, one of the radicals $R_4$, $R_5$, $R_6$, $R_7$ and $R_8$ is a radical of formula II

$$-N(R_9)-C(=X)-(Y)_n-R_{10} \quad (II),$$

wherein $R_9$ is hydrogen or lower alkyl,

X is oxo, thio, imino, N-lower alkyl-imino, hydroximino or O-lower alkyl-hydroximino, Y is oxygen or the group NH, n is 0 or 1 and $R_{10}$ is phenyl which is a) substituted by a radical selected from the group consisting of amino; mono- or di-lower alkylamino; lower alkanoylamino; formyl; lower alkoxy-carbonyl; and lower alkyl which is substituted by amino, mono- or di-lower alkylamino or lower alkanoylamino, or b) substituted by an unsubstituted or substituted radical selected from the group consisting of benzylamino; benzoylamino; pyrrolidinyl; piperidyl; piperazinyl; piperazinyl-carbonyl; morpholinyl; and lower alkyl substituted by benzylamino, benzoylamino, pyrrolidinyl, piperidyl, piperazinyl or morpholinyl, the substituents of said substituted radical being selected from the group consisting of cyano; lower alkyl; hydroxy- or amino-substituted lower alkyl; trifluoromethyl; hydroxy; lower alkoxy; lower alkanoyloxy; amino; mono- or di-lower alkylamino; lower alkanoylamino; benzoylamino; carboxy; lower alkoxycarbonyl and halogen, and c) optionally further substituted by one or more radicals selected from the group consisting of cyano; lower alkyl; hydroxy- or amino-substituted lower alkyl; trifluoromethyl; hydroxy; lower alkoxy; lower alkanoyloxy; amino; mono- or di-lower alkylamino; lower alkanoylamino; benzoylamino; carboxy; lower alkoxycarbonyl and halogen, with the proviso that $R_{10}$ is not (4-methyl-piperazinyl)-methylphenyl, and the remaining radicals $R_4$, $R_5$, $R_6$, $R_7$ and $R_8$ are each independently of the others hydrogen; lower alkyl that is unsubstituted or substituted by free or alkylated amino, piperazinyl, piperidyl, pyrrolidinyl or morpholinyl; lower alkanoyl; trifluoromethyl; free, etherified or esterifed hydroxy; free, alkylated or acylated amino; or free or esterified carboxy, or a salt of such a compound having at least one salt-forming group.

1-Methyl-1H-pyrrolyl $R_1$ is preferably 1-methyl-1H-pyrrol-2-yl or 1-methyl-1H-pyrrol-3-yl Amino- or amino-lower alkyl-substituted phenyl $R_1$ wherein the amino group in each case is free, alkylated or acylated is phenyl substituted in any desired position (ortho, meta or para) wherein an alkylated amino group is preferably mono- or di-lower alkylamino, for example dimethylamino, and the lower alkyl moiety of amino-lower alkyl is preferably linear $C_1$-$C_3$alkyl, such as especially methyl or ethyl.

1H-Indolyl $R_1$ bonded at a carbon atom of the five-membered ring is 1H-indol-2-yl or 1H-indol-3-yl Unsubstituted or lower alkyl-substituted pyridyl $R_1$ bonded at a ring carbon atom is lower alkylsubstituted or preferably unsubstituted 2-, 4- or preferably 3-pyridyl, for example 3-pyridyl, 2-methyl-3-pyridyl or 4-methyl-3-pyridyl. Pyridyl substituted at the nitrogen atom by oxygen is a radical derived from pyridine N-oxide, i.e. N-oxido-pyridyl.

When X is oxo, thio, imino, N-lower alkyl-imino, hydroximino or O-lower alkyl-hydroximino, the group C=X is, in the above order, a radical C=O, C=S, C=N—H, C=N-lower alkyl, C=N—OH or C=N—O-lower alkyl, respectively. X is preferably oxo.

n is preferably 0, i.e. the group Y is not present.

Y, if present, is preferably the group NH.

The term "lower" within the scope of this text denotes radicals having up to and including 7, preferably up to and including 4-carbon atoms.

Lower alkyl $R_2$, $R_3$ and $R_9$ is preferably methyl or ethyl.

A radical selected from the above-mentioned list a) or b) is preferably bonded to phenyl $R_{10}$ at postion 3 or 4 of the phenyl ring.

Phenyl $R_{10}$ substituted by unsubstituted or substituted pyrrolidinyl-, piperidyl-, piperazinyl- or morpholinyl-lower alkyl is preferably phenyl $R_{10}$ substituted by unsubstituted or substituted 1-pyrrolidinyl-, 1-piperidyl-, piperazin-1-yl- or morpholin-4-yl-lower alkyl, respectively.

Phenyl $R_{10}$ substituted by unsubstituted or substituted pyrrolidinyl-, piperidyl-, piperazinyl- or morpholinyl-lower alkyl is preferably phenyl $R_{10}$ substituted by unsubstituted or substituted pyrrolidinyl-, piperidyl-, piperazinyl- or morpholinyl-methyl, respectively.

Etherified hydroxy is preferably lower alkoxy. Esterified hydroxy is preferably hydroxy esterified by an organic carboxylic acid, such as a lower alkanoic acid, or a mineral acid, such as a hydrohalic acid, for example lower alkanoyloxy or especially halogen, such as iodine, bromine or especially fluorine or chlorine.

Alkylated amino is, for example, lower alkylamino, such as methylamino, or di-lower alkylamino, such as dimethylamino. Acylated amino is, for example, lower alkanoylamino or benzoylamino.

Esterified carboxy is, for example, lower alkoxycarbonyl, such as methoxycarbonyl.

Salt-forming groups in a compound of formula I are groups or radicals having basic or acidic properties. Compounds having at least one basic group or at least one basic radical, for example a free amino group, a pyrazinyl radical or a pyridyl radical, may form acid addition salts, for example with inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxy-benzoic acid, 2-acetoxy-benzoic acid, salicylic acid, 4-aminosalicylic acid, aromaticaliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxyethane-sulfonic acid, or aromatic sulfonic acids, for example benzene-, p-toluene- or naphthalene-2-sulfonic acid. When several basic groups are present mono- or poly-acid addition salts may be formed.

Compounds of formula I having acidic groups, for example a free carboxy group in the radical $R_{10}$, may form metal or ammonium salts, such as alkali metal or alkaline earth metal salts, for example sodium, potassium, magnesium or calcium salts, or ammonium salts with ammonia or suitable organic amines, such as tertiary monoamines, for example triethyl-amine or tri-(2-hydroxyethyl)-amine, or heterocyclic bases, for example N-ethyl-piperidine or N,N'-dimethylpiperazine.

Compounds of formula I having both acidic and basic groups can form internal salts.

For the purposes of isolation or purification, as well as in the case of compounds that are used further as intermediates, it is also possible to use pharmaceutically unacceptable salts. Only pharmaceutically acceptable, non-toxic salts are used for therapeutic purposes, however, and those salts are therefore preferred.

Owing to the close relationship between the novel compounds in free form and in the form of their salts, including those salts that can be used as intermediates, for example in the purification of the novel compounds or for the identification thereof, hereinbefore and hereinafter any reference to the free compounds should be understood as including the corresponding salts, where appropriate and expedient.

A compound of formula I possesses valuable pharmacological properties and may, for example, be used as an anti-tumour agent, as an agent to treat atherosclerosis, as an agent to treat restenosis, for the prevention of transplantation-induced disorders, such as obliterative bronchiolitis, and/or for preventing the invasion of warm-blooded animal cells by certain bacteria, such as *Porphyromonas gingivalis*.

The phosphorylation of proteins has long been known as an essential step in the differentiation and division of cells. Phosphorylation is catalysed by protein kinases subdivided into serine/threonine and tyrosine kinases. The tyrosine kinases include PDGF (Platelet-derived Growth Factor) receptor tyrosine kinase.

PDGF is a very commonly occurring growth factor, which plays an important role both in normal growth and also in pathological cell proliferation, such as is seen in carcinogenesis and in diseases of the smooth-muscle cells of blood vessels, for example in atherosclerosis and thrombosis.

The inhibition of PDGF-stimulated receptor tyrosine kinase activity in vitro is measured in PDGF receptor immune complexes of A431 cells, as described by E. Andrejauskas-Buchdunger and U. Regenass in Cancer Research 52, 5353-5358 (1992). A compound of formula I inhibits PDGF-dependent acellular receptor phosphorylation. The inhibition of PDGF receptor tyrosine kinase is measured in a microtitre ELISA assay (cf Trinks et al., J. Med. Chem. 37, 1015-27 (1994). A compound of formula I inhibits the tyrosine kinase activity of the PDGF receptor at an $IC_{50}$ (concentration at which activity is inhibited by 50% compared with the control) of between 1 nM and 1 μM, especially between 3 nM and 300 nM.

The inhibition of PDGF receptor tyrosine kinase makes a compound of formula I also suitable for the treatment of tumour diseases, such as gliomas, sarcomas, prostate tumours, and tumours of the colon, breast, and ovary.

A compound of formula I also inhibits cellular processes involving the so-called stem-cell factor (SCF, also known as the c-kit ligand or steel factor), such as SCF receptor (kit) autophosphorylation and the SCF-stimulated activation of MAPK kinase (mitogen-activated protein kinase).

A compound of formula I thus inhibits also the autophosphorylation of SCF receptor (and c-kit, a proto-oncogen). MO7e cells are a human promegakaryocytic leukaemia cell line which depends on SCF for proliferation. They are obtained from Grover Bagby, Oregon Health Sciences University, USA. The cells are cultivated in RPMI 1649 medium supplemented with 10 FBS and 2.5 ng/ml GC-CMF. GM-SCF and SCF are commercially available. Serum-deprived MO7e cells are prepared and incubated for 90 min at 37° C. with the test substance before being stimulated with recombinant SCF for 10 min at 37° C. Identical quantities of cell lysates are analysed by Western blot using antiphosphotyrosine antibodies (Buchdunger et al., Proc. Natl. Acad. Sci (USA) 92, 2558-62 (1995)). The immunodecorated proteins are detected by means of the ECL Western blotting system from Amersham (Amersham, UK). A compound of formula I inhibits the autophosphorylation of the SCF receptor in the micromolar range.

On the basis of the described properties, a compound of formula I may be used not only as a tumour-inhibiting substance, for example in small cell lung cancer, but also as an agent to treat non-malignant proliferative disorders, such as atherosclerosis, thrombosis, psoriasis, scleroderma, and fibrosis, as well as for the protection of stem cells, for example to combat the haemotoxic effect of chemotherapeutic agents, such as 5-fluoruracil, and in asthma. It may especially be used for the treatment of diseases which respond to an inhibition of the PDGF receptor kinase.

In addition, a compound of formula I prevents the development of multidrug resistance in cancer therapy with other chemotherapeutic agents or abolishes a pre-existing resistance to other chemotherapeutic agents. Also regardless of the effect described hereinbefore, a compound of formula I may be used to advantage in combination with other antitumour agents.

Also abl kinase, especially v-abl kinase, is inhibited by a compound of formula I. The inhibition of v-abl tyrosine kinase is determined by the methods of N. Lydon et al, Oncogene Research 5, 161-173 (1990) and J. F. Geissler et al., Cancer Research 52, 4492-8 (1992). In those methods [Val$^5$]-angiotensin II and [γ$^{-32}$P]-ATP are used as substrates.

By analogy, a compound of formula I also inhibits BCR-abl kinase (see Nature Medicine 2, 561-566 (1996)) and is thus suitable for the treatment of BCR-abl-positive cancer and tumour diseases, such as leukaemias (especially chronic myeloid leukaemia and acute lymphoblastic leukaemia, where especially apoptotic mechanisms of action are found), and also shows effects on the subgroup of leukaemic stem cells as well as potential for the purification of these cells in vitro after removal of said cells (for example, bone marrow removal) and reimplantation of the cells once they have been cleared of cancer cells (for example, reimplantation of purified bone marrow cells).

In addition, a compound of formula I shows useful effects in the treatment of disorders arising as a result of transplantation, for example, allogenic transplantation, especially tissue rejection, such as especially obliterative bronchiolitis (OB), i.e. a chronic rejection of allogenic lung transplants. In contrast to patients without OB, those with OB often show an elevated PDGF concentration in bronchoalveolar lavage fluids. If a compound of formula I is administered to rats with tracheal allogenic transplants, for example in a dose of 50 mg/kg i.p., it can be shown after removal of 10 transplants per group after 10 and 30 days for morphometric analysis of possible epithelial lesions and occlusion of the airways, and investigation for immunohistochemical pathways of action that, although a compound of formula I has no significant effect on epithelial necrosis or infiltration by inflammatory cells, it does markedly reduce fibroproliferation and occlusion of the lumen compared with controls. Synergistic effects with other immunomodulatory or anti-inflammatory substances are possible, for example when used in combination with cyclosporin A (CsA), rapamycin, or ascomycin, or immunosuppressant analogues thereof, for example cyclosporin G, FK-506 or comparable compounds; corticosteroids; cyclophosphamide; azathioprine; methotrexate; brequinar; leflunomide; mizoribine; mycophenolic acid; mycophenolate mofetil; 15-deoxyspergualin; immunsuppressant antibodies, especially monoclonal antibodies for leucocyte receptors, for example MHC, CD2, CD3, CD4, CD7, CD25, CD28, B7, CD45, CD58 or their ligands; or other immunomodulatory compounds, such as CTLA4Ig. If CsA (1 mg/kg s.c.), for example, is combined with a compound of formula I (50 mg/kg), synergism may be observed.

A compound of formula I is also effective in diseases associated with vascular smooth-muscle cell migration and proliferation (where PDGF and PDGF receptor often also play a role), such as restenosis and atherosclerosis. These effects and the consequences thereof for the proliferation or migration of vascular smooth-muscle cells in vitro and in vivo can be demonstrated by administration of a compound of formula I and also by investigating its effect on the thickening of the vascular intima following mechanical injury in vivo.

A compound of formula I is used in 0.1 N HCl or DMSO at a concentration of 10 mM for in vitro studies. The stock solution is further diluted with cell culture medium and used in concentrations of 10 to 0.1 µM for the experiments. For in vivo administration, a compound of formula I is dissolved for example in DMSO at a concentration of 200 mg/ml and then diluted 1:20 with 1% Tween in 0.9% saline solution. After sonication, a clear solution is obtained. The stock solutions are prepared fresh each day before administration. (The compound of formula I may also be dissolved simply in deionised water for oral administration or in 0.9% saline solution for parenteral administration). Administration is carried out 24 hours before the operation. A compound of formula I is administered to rats in one dose of 50 mg/kg i.p. per day for the entire observation period. Control rats are given the same formulation but without the presence of a compound of formula I. Oral administration is also possible.

Primary cultures of smooth-muscle aorta cells are isolated from 9 to 11-day-old DA (AG-B4, RT1a) rat aorta using a modification of the method described by Thyberg et al. (see Differentiation 25, 156-67 (1983)). The aorta is opened by means of a longitudinal incision and the endothelium carefully removed. The adventitia and the tunica media are separated, and the tunica media is digested with 0.1% collagenase and DNAse in phosphate-buffered physiological saline for 30 min at 37° C. The cells are centrifuged, suspended in culture medium, and then allowed to grow on plastic vials. The primary cells are used for the experiments after passages 2 to 6. Subcultures are kept in DMEM (Dulbecco's Modified Eagle's Medium), supplemented with 10% fetal calf serum, 2 mmol/ml glutamine, 100 mmol/ml streptomycin, and 100 IU/ml penicillin. For identification purposes, the cells are left to grow on glass slide covers and stained immunohistochemically using an anti-α-actin antibody obtained from smooth-muscle cells (see below).

The migration of smooth-muscle cells is quantified in vitro using a Transwell cell culture insert (Costar, Cambridge, Mass.) whose upper and lower compartments are separated by a polycarbonate membrane of 8 µm pore size. The cells (100 µl at a concentration of 1 million cells/ml) are exposed in the upper compartment. After 2 hours, 60 ng/ml PDGF-BB or PDGF-AA (Upstate Biotechnology Inc., Lake Placid, N.Y.) is added to the lower compartment, supplemented with 0.5% fetal calf serum and 0.1% bovine serum albumin, and the test compound of formula I is added in concentrations of 3, 1, 0.3, 0.1, 0.03, 0.01, and 0.003 µM. To measure fibronectin-dependent migration, the Transwell chambers are covered with fibronectin at a concentration of 10 µg/ml for 24 h at 4° C. (human cellular fibronectin, Upstate Biotechnology Inc.). After 24 hours' migration, the filters are removed, fixed in methanol, and stained with Mayer's haematoxylin and eosin. The migrated cells on the lower side of the filter membrane are determined by counting the specified sectional fields on the filters with the aid of a light microscope with a magnification of 400×. The inhibition of migration is quantified in terms of the percentage of cells versus with the control. To exclude the possibility of a toxic effect, the viability of the cells is tested by incorporation of 3H-thymidine in DMEM, supplemented with 10% fetal calf serum. An inhibition of migration induced by PDGF-AA and especially by PDGF-BB is observed with a compound of formula I.

Experimental animals: the aorta and carotid artery of male Wistar rats (purchased from the Laboratory Animal Center of the University of Helsinki, Finland) are denuded. The rats are anaesthetised with 240 mg/kg chloral hydrate i.p. and Buprenorphine (Temgesic, Reckitt & Coleman, Hull, UK) is administered for perioperative and postoperative alleviation of pain. All animals are given human care in keeping with the "Principles of Laboratory Animal Care" and the "Guide for the Care and Use of Laboratory Animals" of the NIH (NIH Publication 86-23, revised 1985). Rats weighing 200-300 g were used for the denudation procedure. The left common carotid artery is denuded of endothelium through the intraluminal passage of a 2F embolectomy catheter (Baxter Healthcare Corporation, Santa Ana, Calif., 27). To remove the endothelium, the catheter is passed through the lumen three times, inflated with 0.2 ml air. The external carotid is ligated after removal of the catheter and the wound closed. The histological changes are evaluated by reference to sections of mid-carotid 4 days after denudation. The thoracic aorta is denuded of endothelium using a 2F Fogarty arterial embolectomy catheter. The catheter is inserted into the thoracic aorta via the left iliac artery, inflated with 0.2 ml air, and passed through the lumen five times to remove the endothelium. The iliac artery is then ligated. Three times (3, 7 and 14 days) are selected for evaluation of the histological changes.

To quantify the proliferating cells, 3 different procedures are used for labelling the cells with bromodeoxyuridine (BrdU) after denudation of the rat carotid. In this model, the media cell proliferation begins 24 h after denudation; cells in the intima first appear after 72-96 hours. To quantify the proliferation of smooth-muscle cells before the appearance of cells in the intima, 0.1 ml BrdU-labelling reagent (ZYMED, San Francisco, Calif.) is administered i.v. during the postoperative period of 0 to 72 h post-denudation (in total 0.1 ml 6 times). To quantify the proliferation during the initial wave of migration, the rats were given 3×0.1 ml BrdU-labelling reagent at 8-hour intervals over a period of 72-96 hours after the operation. To quantify the proliferation at the end of the initial wave of migration, a third group of rats is given a pulsed dose of 0.3 ml BrdU three hours before sacrifice.

Histological samples are fixed in 3% paraformaldehyde solution for 4 h for embedding in paraffin. Morphological changes are evaluated from paraffin sections stained with Mayer's haematoxylin-eosin. The cell counts of different vessel sections are calculated at a magnification of 400×. To identify cells in culture and cells appearing in the neo-intima within four days of the denudation injury, immunohistochemical staining of acetone-fixed samples is carried out using an anti-α-actin antibody obtained from smooth-muscle cells (Bio-Makor, Rehovot, Israel). Primary smooth-muscle cells are identified on acetone-fixed glass cover slides using the same staining method. The sections are incubated with the primary antibody (dilution 1:2000), washed, and incubated consecutively with peroxidase-conjugated rabbit-antimouse-Ig and goat-antirabbit-Ig, followed by treatment with substrate solution with the chromogen 3-amino-9-ethylcarbazol and hydrogen peroxide. BrdU stains are prepared from paraffin sections using a primary mouse antibody (Bu20a, Dako, A/S, Denmark) and the Vectastain Elite ABC-Kit (Vector Laboratories, Burliname, Calif.). The sections are deparaffinised and treated by microwave at 500 W (2×5 min in 0.1M citrate buffer, pH 6), followed by treatment with 95% formamide in 0.15 M trisodium citrate for 45 min at 70° C. Antibody dilutions are prepared according to the manufacturer's specifications. The sections are counterstained with Mayer's haematoxylin and eosin, and positive cells are counted separately for the initima, media, and adventitia.

In the carotid of treated animals, a significant decrease is found in the cell count for smooth-muscle cells. The adventitia and the media showed a significant reduction in the cell count. As a result of a compound of formula I, a slight decrease in the absolute number of BrdU-labelled cells is seen in the intima, media, and adventitia during the first two labelling periods (0-72 and 72-96 h), and after 93-96 h a decrease in the number of labelled cells is seen in all compartments. Decreases in the number of smooth-muscle cells are likewise found in the aorta-denuded animals.

According to these findings, a compound of formula I can thus inhibit the proliferation, and especially the migration, of vascular smooth-muscle cells.

A compound of formula I is also capable of inhibiting angiogenesis. This may be demonstrated as follows: a chamber containing agar (0.8%) and heparin (2 U/ml) with or without growth factor (VEGF 3 µg/ml, PDGF 1 µg/ml or bFGF 0.3 µg/ml) is implanted subcutaneously into normal mice (C57 BL/6). A compound of formula I is administered orally in a dose showing good anti-tumour activity in a nude mouse xenotransplant model. Dosing is started one day before implantation of the chambers. The chambers are removed after 5 days. The angiogenic efficacy is quantified by measuring both the vascularised tissue which has grown around the implant and the blood content of this tissue (external blood). The blood is determined by measuring the haemoglobin. Although the vessels do not grow into the agar, the agar becomes intensely red if an antiangiogenic effect is present. If a compound inhibits the increase in blood that is induced by the growth factor, this is seen as an indication that the compound in question is blocking the angiogenic effect of the growth factor concerned. Inhibition of the weight but not the volume of blood suggests an effect on the proliferation of fibroblasts. A suppression of the control response suggests an inhibition of wound healing. At an oral dose of 50 mg/kg once daily, a compound of formula I inhibits the angiogenic effect of all three growth factors (VEGF, PDFG, bFGF).

Interestingly, N-[4-methyl-3-(4-pyridin-3-yl-pyrimidin-2-ylamino)-phenyl]-4-piperazin-1-ylmethyl-benzamide represents the N-desmethyl metabolite of N-[4-methyl-3-(4-pyridin-3-yl-pyrimidin-2-ylamino)-phenyl]-4-(4-methyl-piperazin-1-ylmethyl)-benzamide (STI571). STI571 is described in EP 0 564 409 and, in the form of the methane sulfonate salt, in WO 99/03854. The N-desmethyl metabolite of STI571 is an active metabolite that is present in human plasma at concentrations from 30 to 50% of STI571 and the half-life is somewhat longer than that of STI571. Moreover, the N-desmethyl metabolite exhibits less inhibition of certain cytochrome P450 enzymes (see following paragraph), when compared with STI571. Cytochromes P450 are the principal, hepatic xenobiotic metabolizing enzymes and less inhibition of cytochromes P450 reduces the potential of a compound for clinical drug-drug interactions. Among the compounds of formula I, preference above all is therefore given for the N-desmethyl metabolite of STI571, namely N-[4-methyl-3-(4-pyridin-3-yl-pyrimidin-2-ylamino)-phenyl]-4-piperazin-1-ylmethyl-benzamide.

In order to evaluate the effect of the compounds of formula I on cytochromes P450 (CYPs), e.g. enzyme inhibition is routinely assessed by performing in vitro inhibition studies using cDNA-expressed enzymes or human liver microsomes (Parkinson, A., Toxicol. Pathol. 24, 45-57 [1996]). Specific drug marker substrate assays according to Tucker et al., Clin. Pharmacol. Ther. 70, 103-114 (2001) can be used to determine the 50% inhibition concentration ($IC_{50}$) of a compound of formula I for the principal drug-metabolizing P450 enzymes such as e.g. CYP1A2, CYP2A6, CYP2B6, CYP2C8, CYP2C9, CYP2C19, CYP2D6, CYP2E1, CYP3A4/5 and CP4A9/11.

Inhibition constants Ki or $IC_{50}$ values derived by these in vitro assays provide a measure for the inhibition capacity of the tested drug compound according to the ratio of drug concentration in plasma to the respective inhibition constant Ki, where a ratio of >1.0 results in a high risk, 1.0-0.1 in a medium risk, and <0.1 In a low risk of metabolic drug interaction. Based on this, N-[4-methyl-3-(4-pyridin-3-yl-pyrimidin-2-ylamino)-phenyl]-4-piperazin-1-ylmethyl-benzamide possesses a much lower risk of drug-drug interactions with the 2 most important P450 enzymes, CYP2D6 and CYP3A4/5, in human drug metabolism (see guidance document of the U.S. Food and Drug Administration) when compared with STI571.

Preference is given to compounds of formula I, wherein $R_1$ is unsubstituted or lower alkyl-substituted pyridyl bonded at a ring carbon atom and unsubstituted or substituted at the nitrogen atom by oxygen, $R_2$ and $R_3$ are each independently of the other hydrogen or lower alkyl, one of the radicals $R_4$, $R_5$, $R_6$, $R_7$ and $R_8$ is a radical of formula II, wherein $R_9$ is hydrogen or lower alkyl, X is oxo, thio, imino, N-lower alkyl-imino, hydroximino or O-lower alkyl-hydroximino, n is 0 and $R_{10}$ is phenyl which is
  a) substituted by a radical selected from the group consisting of amino; mono- or di-lower alkylamino; lower alkanoylamino; formyl; lower alkoxy-carbonyl; and lower alkyl which is substituted by amino, mono- or di-lower alkylamino or lower alkanoylamino, or
  b) substituted by an unsubstituted or substituted radical selected from the group consisting of benzylamino; benzoylamino; pyrrolidinyl; piperidyl; piperazinyl; piperazinyl-carbonyl; morpholinyl; and lower alkyl substituted by benzylamino, benzoylamino, pyrrolidinyl, piperidyl, piperazinyl or morpholinyl, the substituents of said substituted radical being selected from the group consisting of cyano; lower alkyl; hydroxy- or amino-substituted lower alkyl; trifluoromethyl; hydroxy; lower alkoxy; lower alkanoyloxy; amino; mono- or di-lower alkylamino; lower alkanoylamino; benzoylamino; carboxy; lower alkoxycarbonyl and halogen, and
  c) optionally further substituted by one or more radicals selected from the group consisting of cyano; lower alkyl; hydroxy- or amino-substituted lower alkyl; trifluoromethyl; hydroxy; lower alkoxy; lower alkanoyloxy; amino; mono- or di-lower alkylamino; lower alkanoylamino; benzoylamino; carboxy; lower alkoxycarbonyl and halogen, with the proviso that $R_{10}$ is not (4-methyl-piperazinyl)-methylphenyl, and the remaining radicals $R_4$, $R_5$, $R_6$, $R_7$ and $R_8$ are each independently of the others hydrogen; lower alkyl that is unsubstituted or substituted by free or alkylated amino, piperazinyl, piperidyl, pyrrolidinyl or morpholinyl; lower alkanoyl; trifluoromethyl; free, etherified or esterifed hydroxy; free, alkylated or acylated amino; or free or esterified carboxy, or a salt of such a compound having at least one salt-forming group.

Preference is also given to compounds of formula I, wherein $R_1$ is unsubstituted or lower alkyl-substituted pyridyl bonded at a ring carbon atom and unsubstituted or substituted at the nitrogen atom by oxygen, $R_2$ and $R_3$ are each independently of the other hydrogen or lower alkyl, $R_5$ or $R_7$ is a radical of formula II, wherein $R_9$ is hydrogen, X is oxo, n is 0 and $R_{10}$ is phenyl which is
  a) substituted by a radical selected from the group consisting of amino; mono- or di-lower alkylamino; lower alkanoylamino; formyl; lower alkoxy-carbonyl; and lower alkyl which is substituted by amino, mono- or di-lower alkylamino or lower alkanoylamino, or
  b) substituted by an unsubstituted or substituted radical selected from the group consisting of benzylamino; benzoylamino; pyrrolidinyl; piperidyl; piperazinyl; piperazinyl-carbonyl; morpholinyl; and lower alkyl substituted by benzylamino, benzoylamino, pyrrolidinyl, piperidyl, piperazinyl or morpholinyl, the substituents of said substituted radical being selected from the group consisting of cyano; lower alkyl; hydroxy- or amino-substituted lower alkyl; trifluoromethyl; hydroxy; lower alkoxy; lower alkanoyloxy; amino; mono- or di-lower alkylamino; lower alkanoylamino; benzoylamino; carboxy; lower alkoxycarbonyl and halogen, or
  c) substituted by piperazinyl-lower alkyl which is optionally substituted by one or more radicals selected from the group consisting of cyano; $C_3$-$C_7$-lower alkyl; hydroxy- or amino-substituted lower alkyl; trifluoromethyl; hydroxy; lower alkoxy; lower alkanoyloxy; amino; mono- or di-lower alkylamino; lower alkanoylamino; benzoylamino; carboxy; lower alkoxycarbonyl and halogen, and
  d) optionally further substituted by one or more radicals selected from the group consisting of cyano; lower alkyl; hydroxy- or amino-substituted lower alkyl; trifluoromethyl; hydroxy; lower alkoxy; lower alkanoyloxy; amino; mono- or di-lower alkylamino; lower alkanoylamino; benzoylamino; carboxy; lower alkoxycarbonyl and halogen, and the remaining radicals $R_4$, $R_5$, $R_6$, $R_7$ and $R_8$ are each independently of the others hydrogen; lower alkyl that is unsubstituted or substituted by free or alkylated amino, piperazinyl, piperidyl, pyrrolidinyl or morpholinyl; lower alkanoyl; trifluoromethyl; free, etherified or esterifed hydroxy; free, alkylated or acylated amino; or free or esterified carboxy, or a salt of such a compound having at least one salt-forming group.

Special preference is given to compounds of formula I, wherein $R_1$ is unsubstituted or lower alkyl-substituted pyridyl bonded at a ring carbon atom and unsubstituted or substituted at the nitrogen atom by oxygen, $R_2$ and $R_3$ are both hydrogen, $R_4$ is lower alkyl, $R_5$ and $R_6$ are both hydrogen, $R_7$ is a radical of formula II, wherein $R_9$ is hydrogen, X is oxo, n is 0 and $R_{10}$ is phenyl which is
  a) substituted by a radical selected from the group consisting of amino; mono- or di-lower alkylamino; lower alkanoylamino; formyl; lower alkoxy-carbonyl; and lower alkyl which is substituted by amino, mono- or di-lower alkylamino or lower alkanoylamino, or b) substituted by an unsubstituted or substituted radical selected from the group consisting of benzylamino; benzoylamino; pyrrolidinyl; piperidyl; piperazinyl; piperazinyl-carbonyl; morpholinyl; and lower alkyl substituted by benzylamino, benzoylamino, pyrrolidinyl, piperidyl or morpholinyl, the substituents of said substituted radical being selected from the group consisting of cyano; lower alkyl; hydroxy- or amino-substituted lower alkyl; trifluoromethyl; hydroxy; lower alkoxy; lower alkanoyloxy; amino; mono- or di-lower alkylamino; lower alkanoylamino; benzoylamino; carboxy; lower alkoxycarbonyl and halogen, or c) substituted by piperazinyl-lower alkyl which is optionally substituted in the piperazine ring by one or more radicals selected from the group consisting of cyano; $C_3$-$C_7$-lower alkyl; hydroxy- or amino-substituted lower alkyl; trifluoromethyl; hydroxy; lower alkoxy; lower alkanoyloxy; amino; mono- or di-lower alkylamino; lower alkanoylamino; benzoylamino; carboxy; lower alkoxycarbonyl and halogen, and $R_8$ is hydrogen, or a salt of such a compound having at least one salt-forming group.

Special preference is given especially to compounds of formula I, wherein $R_1$ is unsubstituted or lower alkyl-substituted pyridyl bonded at a ring carbon atom and unsubstituted or substituted at the nitrogen atom by oxygen, $R_2$ and $R_3$ are both hydrogen, $R_4$ is lower alkyl, $R_5$ and $R_6$ are both hydrogen, $R_7$ is a radical of formula II, wherein $R_9$ is hydrogen, X is oxo, n is 0 and $R_{10}$ is phenyl which is a) substituted by lower alkyl that is substituted by amino, mono- or di-lower alkylamin or lower alkanoylamino, or b) substituted by an unsubstituted or substituted radical selected from the group consisting of benzylamino; benzoylamino; pyrrolidinyl; piperidyl; piperazinyl; piperazinyl-carbonyl; morpholinyl; and lower alkyl substituted by benzylamino, benzoylamino, pyrrolidinyl, piperidyl or morpholinyl, the substituents of said substituted radical being selected from the group consisting of cyano; lower alkyl; hydroxy- or amino-substituted lower alkyl; trifluoromethyl; hydroxy; lower alkoxy; lower alkanoyloxy; amino; mono- or di-lower alkylamino; lower alkanoylamino; benzoylamino; carboxy; lower alkoxycarbonyl and halogen, or c) substituted by piperazinyl-lower alkyl which is optionally substituted in the piperazine ring by one or more radicals selected from the group consisting of cyano; $C_3$-$C_7$-lower alkyl; hydroxy- or amino-substituted lower alkyl; trifluoromethyl; hydroxy; lower alkoxy; lower alkanoyloxy; amino; mono- or di-lower alkylamino; lower alkanoylamino; benzoylamino; carboxy; lower alkoxycarbonyl and halogen, and $R_8$ is hydrogen, or a salt of such a compound having at least one salt-forming group.

Very special preference is given to compounds of formula I, wherein $R_1$ is pyridyl bonded at a ring carbon atom, $R_2$ and $R_3$ are both hydrogen, $R_4$ is lower alkyl, $R_5$ and $R_6$ are both hydrogen, $R_7$ is a radical of formula II, wherein $R_9$ is hydrogen, X is oxo, n is 0 and $R_{10}$ is phenyl which is a) substituted by a radical selected from the group consisting of di-lower alkylamino; lower alkanoylamino; and lower alkyl which is substituted by di-lower alkylamino, or b) substituted by pyrrolidinyl-lower alkyl, piperidyl-lower alkyl or morpholinyl-lower alkyl, or c) substituted by piperazinyl-lower alkyl which is optionally substituted in the piperazine ring by $C_3$-$C_7$-lower alkyl or by 2 to 5 lower alkyl radicals, and $R_8$ is hydrogen, or a salt of such a compound having at least one salt-forming group.

Also very special preference is given to compounds of formula I, wherein $R_1$ is pyridyl bonded at a ring carbon atom, $R_2$ and $R_3$ are both hydrogen, $R_4$ is lower alkyl, $R_5$ and $R_6$ are both hydrogen, $R_7$ is a radical of formula II, wherein $R_9$ is hydrogen, X is oxo, n is 0 and $R_{10}$ is phenyl which is a) substituted by lower alkyl that is substituted by mono- or di-lower alkylamino, or b) substituted by an unsubstituted or lower alkyl-substituted radical selected from the group consisting of pyrrolidinyl-lower alkyl, piperidyl-lower alkyl and morpholinyl-lower alkyl, or c) substituted by piperazinyl-lower alkyl which is optionally substituted in the piperazine ring by $C_3$-$C_7$-lower alkyl, and $R_8$ is hydrogen, or a salt of such a compound having at least one salt-forming group.

Most especially preferred are the compounds of formula I described in the Examples and pharmaceutically acceptable salts of such compounds having at least one salt-forming group.

The compounds of formula I and salts of such compounds having at least one salt-forming group are prepared in accordance with processes known per se. The process according to the invention is characterized in that:

i) a compound of formula III

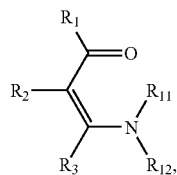
(III)

wherein $R_{11}$ and $R_{12}$ are each independently of the other lower alkyl and $R_1$, $R_2$ and $R_3$ are as defined above, functional groups present in a compound of formula III, with the exception of the groups participating in the reaction, being if necessary in protected form, or a salt of such a compound, is reacted with a compound of formula IV

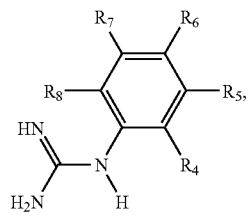
(IV)

wherein the substituents are as defined above, functional groups present in a compound of formula IV, with the exception of the guanidino group participating in the reaction, being if necessary in protected form, or with a salt of such a compound, and any protecting groups present are removed, or ii) a compound of formula V

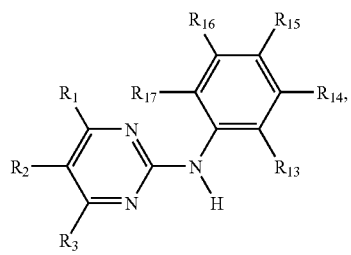
(V)

wherein one of the radicals $R_{13}$, $R_{14}$, $R_{15}$, $R_{16}$ and $R_{17}$ is a radical of the formula —N($R_9$)—H, wherein $R_9$ is as defined above, and the remaining radicals $R_{13}$, $R_{14}$, $R_{15}$, $R_{16}$ and $R_{17}$ are each independently of the others hydrogen; lower alkyl that is unsubstituted or substituted by free or alkylated amino, piperazinyl, piperidyl, pyrrolidinyl or by morpholinyl; lower alkanoyl; trifluoromethyl; free, etherified or esterified hydroxy; free, alkylated or acylated amino; or free or esterified carboxy, and the remaining substituents are as defined above, functional groups present in a compound of formula V, with the exception of the amino group participating in the reaction, being if necessary in protected form, is reacted with a compound of formula VI

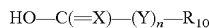
HO—C(=X)—(Y)$_n$—R$_{10}$ (VI), wherein the substituents and symbols are as defined above, functional groups present in a compound of formula VI, with the exception of the HO—C(=X) group participating in the reaction, being if necessary in protected form, or with a reactive derivative of a compound of formula VI, and any protecting groups present are removed, or iii) for the preparation of a compound of formula I wherein $R_1$ is pyridyl substituted at the nitrogen atom by oxygen, and wherein the other substituents and symbols are as defined above, a compound of formula I wherein $R_1$ is pyridyl is converted into the N-oxido compound with a suitable oxidising agent, or iv) for the preparation of a compound of formula I, wherein $R_{10}$ is phenyl which is
  a) substituted by lower alkyl which is itself substituted by mono- or di-lower alkylamino or lower alkanoylamino, or
  b) substituted by an unsubstituted or substituted radical selected from the group consisting of benzylamino-, benzoylamino-, pyrrolidinyl-, piperidyl-, piperazinyl- and morpholinyl-lower alkyl, the substituents of said substituted radical being selected from the group consisting of cyano; lower alkyl; hydroxy- or amino-substituted lower alkyl; trifluoromethyl; hydroxy; lower alkoxy; lower alkanoyloxy; amino; mono- or di-lower alkylamino; lower alkanoylamino; benzoylamino; carboxy; lower alkoxycarbonyl and halogen, and
  c) optionally further substituted by one or more radicals selected from the group consisting of cyano; lower alkyl; hydroxy- or amino-substituted lower alkyl; trifluoromethyl; hydroxy; lower alkoxy; lower alkanoyloxy; amino; mono- or di-lower alkylamino; lower alkanoylamino; benzoylamino; carboxy; lower alkoxycarbonyl and halogen, with the proviso that $R_{10}$ is not (4-methyl-piperazinyl)-methylphenyl, a compound of formula VII

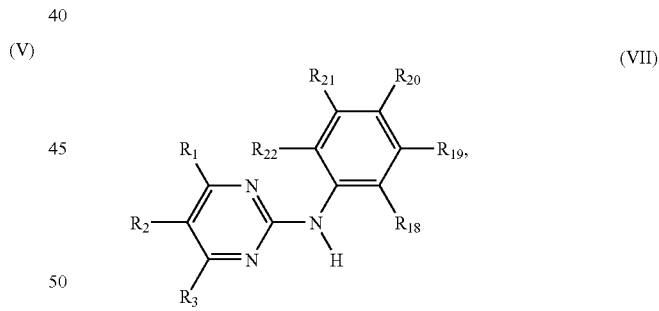
(VII)

wherein $R_1$, $R_2$ and $R_3$ are as defined above and one of the radicals $R_{18}$, $R_{19}$, $R_{20}$, $R_{21}$ and $R_{22}$ is a radical of formula VIII

—N($R_9$)—C(=X)—(Y)$_n$—R$_{23}$ (VIII), wherein $R_{23}$ is halogen-lower alkyl-phenyl that is optionally substituted by one or more radicals selected from the group consisting of cyano; lower alkyl; hydroxy- or amino-substituted lower alkyl; trifluoromethyl; hydroxy; lower alkoxy; lower alkanoyloxy; amino; mono- or di-lower alkylamino; lower alkanoylamino; benzoylamino; carboxy; lower alkoxycarbonyl and halogen, and n, $R_9$, X and Y are as defined above, and the remaining radicals $R_{18}$, $R_{19}$, $R_{20}$, $R_{21}$ and $R_{22}$ are each independently of the others hydrogen;

lower alkyl that is unsubstituted or substituted by free or alkylated amino, piperazinyl, piperidyl, pyrrolidinyl or by morpholinyl; lower alkanoyl; trifluoromethyl; free, etherified or esterified hydroxy; free, alkylated or acylated amino; or free or esterified carboxy, functional groups present in a compound of formula VII, with the exception of the groups participating in the reaction, being if necessary in protected form, is reacted with a reactant selected from mono- or di-lower alkylamine and lower alkanoylamine, or with an unsubstituted or substituted reactant selected from the group consisting of benzylamine, benzoylamine, pyrrolidine, piperidine, piperazine and morpholine, the substituents being selected from the group consisting of cyano; lower alkyl; hydroxy- or amino-substituted lower alkyl; trifluoromethyl; hydroxy; lower alkoxy; lower alkanoyloxy; amino; mono- or di-lower alkylamino; lower alkanoylamino; benzoylamino; carboxy; lower alkoxycarbonyl and halogen, with the proviso that the reactant is not 4-methyl-piperazine if $R_{23}$ is unsubstituted halogen-methyl-phenyl, functional groups present in a reactant, with the exception of the groups participating in the reaction, being if necessary in protected form, and any protecting groups present are removed, and, if desired, a compound of formula I obtainable by any one of processes i) to iv) is converted into its salt, or an obtainable salt of a compound of formula I is converted into the free compound.

The procedure for the above-mentioned process variants is explained in detail below:

General Notes:

The end products of formula I may contain substituents that can also be used as protecting groups in starting materials for the preparation of other end products of formula I. Thus, within the scope of this text, only a readily removable group that is not a constituent of the particular desired end product of formula I is designated a "protecting group", unless the context indicates otherwise.

Protecting groups, and the manner in which they are introduced and removed are described, for example, in "Protective Groups in Organic Chemistry", Plenum Press, London, New York 1973, and in "Methoden der organischen Chemie", Houben-Weyl, 4th edition, Vol. 15/1, Georg-Thieme-Verlag, Stuttgart 1974 and in Theodora W. Greene, "Protective Groups in Organic Synthesis", John Wiley & Sons, New York 1981. A characteristic of protecting groups is that they can be removed readily, i.e. without the occurrence of undesired secondary reactions, for example by solvolysis, reduction, photolysis or alternatively under physiological conditions.

Process i):

Preferably $R_{11}$ and $R_{12}$ are each methyl.

Free functional groups in a compound of formula III that are advantageously protected by readily removable protecting groups are especially amino groups in the radical $R_1$ and the imino group of 1H-indolyl. The latter can be protected, for example, by benzyl.

Free functional groups in a compound of formula IV that are advantageously protected by readily removable protecting groups are especially amino groups, but also hydroxy and carboxy groups.

A salt of a compound of formula IV is preferably an acid addition salt, for example a nitrate or one of the acid addition salts mentioned for the end products of formula I.

The reaction is carried out in a suitable solvent or dispersing agent, for example a suitable alcohol, such as 2-methoxy-ethanol, or a suitable lower alkanol, for example isopropanol, at a temperature of from room temperature (approx. 20° C.) to 150° C., for example under reflux. Especially when the compound of formula IV is used in the form of a salt, that salt is converted into the free compound, preferably in situ by the addition of a suitable base, such as an alkali metal hydroxide, for example sodium hydroxide.

The starting material of formula III is obtained by reacting a compound of formula IX

wherein the substituents are as defined above, with a compound of formula X

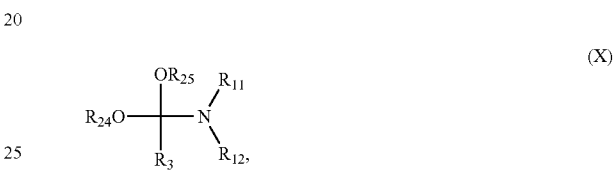

wherein $R_{24}$ and $R_{25}$ are each lower alkyl and the remaining substituents are as defined above, in a manner analogous to that described in the European Patent Application having the Publication No. 233461. Typical representatives of a compound of formula X are N,N-dimethylformamide-dimethylacetal and N,N-dimethylacetamide-dimethylacetal. The reaction is carried out with heating of the reactants of formulae IX and X for several hours, for example for from 4 to 24 hours, at a temperature of approximately from 50° C. to 150° C., in the absence or, if necessary, in the presence of a solvent.

The starting material of formula III is alternatively obtained by reacting a compound of formula IX with an ester of the formula $R_3$—C(=O)—O—CH$_2$—CH$_3$ wherein $R_3$ is as defined above, and reacting the resulting product with an amine of the formula H—N($R_{11}$)—$R_{12}$ wherein the substituents are as defined above.

The starting material of formula IV is obtained in the form of an acid addition salt by reacting a compound of formula XI

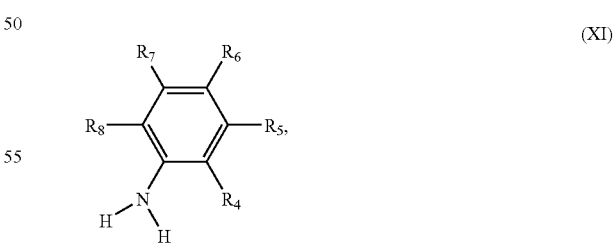

wherein the substituents are as defined above, with cyanamide (NC—NH$_2$). The reaction is carried out in a suitable solvent or dispersing agent, for example a suitable alcohol, for example a suitable lower alkanol, such as ethanol, in the presence of equimolar amounts of the salt-forming acid at a temperature of from room temperature to 150° C., for example under reflux.

Process ii):

Free functional groups in a compound of formula V or VI that are advantageously protected by readily removable protecting groups are especially amino groups, but also hydroxy and carboxy groups, that are not intended to participate in the desired reaction, for example amino in the radical $R_1$.

A reactive derivative of a compound of formula VI wherein X is oxo is especially a reactive (activated) ester, a reactive anhydride or a reactive cyclic amide. The same is true for the derivatives wherein X has one of the other definitions given above.

Reactive (activated) esters of an acid of formula VI are especially esters unsaturated at the linking carbon atom of the esterifying radical, for example esters of the vinyl ester type, such as actual vinyl esters (obtainable, for example, by transesterification of a corresponding ester with vinyl acetate; activated vinyl ester method), carbamoylvinyl esters (obtainable, for example, by treatment of the corresponding acid with an isoxazolium reagent; 1,2-oxazolium or Woodward method), or 1-lower alkoxyvinyl esters (obtainable, for example, by treatment of the corresponding acid with a lower alkoxyacetylene; ethoxy-acetylene method), or esters of the amidino type, such as N,N'-disubstituted amidino esters (obtainable, for example, by treatment of the corresponding acid with a suitable N,N'-disubstituted carbodiimide, for example N,N'-dicyclohexylcarbodiimide; carbodiimide method), or N,N-disubstituted amidino esters (obtainable, for example, by treatment of the corresponding acid with an N,N-disubstituted cyanamide; cyanamide method), suitable aryl esters, especially phenyl esters suitably substituted by electron-attracting substituents (obtainable, for example, by treatment of the corresponding acid with a suitably substituted phenol, for example 4-nitrophenol, 4-methylsulfonyl-phenol, 2,4,5-trichlorophenol, 2,3,4,5,6-pentachloro-phenol or 4-phenyldiazophenol, in the presence of a condensation agent, such as N,N'-dicyclohexylcarbodiimide; activated aryl esters method), cyanomethyl esters (obtainable, for example, by treatment of the corresponding acid with chloroacetonitrile in the presence of a base; cyanomethyl esters method), thio esters, especially unsubstituted or substituted, for example nitro-substituted, phenylthio esters (obtainable, for example, by treatment of the corresponding acid with unsubstituted or substituted, for example nitro-substituted, thiophenols, inter alia by the anhydride or carbodiimide method; activated thiol esters method), amino or amido esters (obtainable, for example, by treatment of the corresponding acid with an N-hydroxy-amino or N-hydroxy-amido compound, for example N-hydroxy-succinimide, N-hydroxy-piperidine, N-hydroxy-phthalimide or 1-hydroxy-benzotriazole, for example by the anhydride or carbodiimide method; activated N-hydroxy esters method), or silyl esters (which are obtainable, for example, by treatment of the corresponding acid with a silylating agent, for example hexamethyl disilazane, and react readily with hydroxy groups but not with amino groups).

Anhydrides of an acid of formula VI may be symmetric or preferably mixed anhydrides of that acid, for example anhydrides with inorganic acids, such as acid halides, especially acid chlorides (obtainable, for example, by treatment of the corresponding acid with thionyl chloride, phosphorus pentachloride or oxalyl chloride; acid chloride method), azides (obtainable, for example, from a corresponding acid ester via the corresponding hydrazide and treatment thereof with nitrous acid; azide method), anhydrides with carbonic acid semiderivatives, such as corresponding esters, for example carbonic acid lower alkyl semiesters (obtainable, for example, by treatment of the corresponding acid with haloformic, such as chloroformic, acid lower alkyl esters or with a 1-lower alkoxycarbonyl-2-lower alkoxy-1,2-dihydroquinoline, for example 1-lower alkoxycarbonyl-2-ethoxy-1,2-dihydroquinoline; mixed O-alkylcarbonic acid anhydrides method), or anhydrides with dihalogenated, especially dichlorinated, phosphoric acid (obtainable, for example, by treatment of the corresponding acid with phosphorus oxychloride; phosphorus oxychloride method), or anhydrides with organic acids, such as mixed anhydrides with organic carboxylic acids (obtainable, for example, by treatment of the corresponding acid with an unsubstituted or substituted lower alkane- or phenylalkane-carboxylic acid halide, for example phenylacetic acid chloride, pivalic acid chloride or trifluoroacetic acid chloride; mixed carboxylic acid anhydrides method) or with organic sulfonic acids (obtainable, for example, by treatment of a salt, such as an alkali metal salt, of the corresponding acid, with a suitable organic sulfonic acid halide, such as lower alkane- or aryl-, for example methane- or p-toluene-sulfonic acid chloride; mixed sulfonic acid anhydrides method), and symmetric anhydrides (obtainable, for example, by condensation of the corresponding acid in the presence of a carbodiimide or of 1-diethylaminopropyne; symmetric anhydrides method).

Suitable cyclic amides are especially amides with five-membered diazacycles of aromatic character, such as amides with imidazoles, for example imidazole (obtainable, for example, by treatment of the corresponding acid with N,N'-carbonyldiimidazole; imidazolide method), or pyrazoles, for example 3,5-dimethyl-pyrazole (obtainable, for example, by way of the acid hydrazide by treatment with acetylacetone; pyrazolide method).

Derivatives of acids of formula VI that can be used as acylating agents can also be formed in situ. For example, N,N'-disubstituted amidino esters can be formed in situ by reacting a mixture of the starting material of formula V and the acid used as acylating agent in the presence of a suitable N,N-disubstituted carbodiimide, for example N,N'-dicyclohexyl-carbodiimide. In addition, amino or amido esters of the acids used as acylating agents can be formed in the presence of the starting material of formula V to be acylated, by reacting a mixture of the corresponding acid and amino starting materials in the presence of an N,N'-disubstituted carbodiimide, for example N,N'-dicyclohexyl-carbodiimide, and an N-hydroxy-amine or N-hydroxy-amide, for example N-hydroxysuccinimide, where appropriate in the presence of a suitable base, for example 4-dimethylamino-pyridine.

The reaction is preferably carried out by reacting a reactive carboxylic acid derivative of a compound of formula VI with a compound of formula V wherein the amino group or hydroxy group participating in the reaction is in free form.

The reaction can be carried out in a manner known per se, the reaction conditions being dependent especially on whether, and if so how, the carboxy group of the acylating agent has been activated, usually in the presence of a suitable solvent or diluent or of a mixture thereof and, if necessary, in the presence of a condensation agent, which, for example when the carboxy group participating in the reaction is in the form of an anhydride, may also be an acid-binding agent, with cooling or heating, for example in a temperature range from approximately −30° C. to approximately +150° C., especially approximately from 0° C. to +100° C., preferably from room temperature (approx. +20° C.) to +70° C., in an open or closed reaction vessel and/or in the atmosphere of an inert gas, for example nitrogen.

Customary condensation agents are, for example, carbodiimides, for example N,N'-diethyl-, N,N'-dipropyl-, N,N'-dicyclohexyl- or N-ethyl-N'-(3-dimethylaminopropyl)-carbodiimide, suitable carbonyl compounds, for example carbonyldiimidazole, or 1,2-oxazolium compounds, for example 2-ethyl-5-phenyl-1,2-oxazolium 3'-sulfonate and 2-tert-butyl-5-methyl-isoxazolium perchlorate, or a suitable acylamino compound, for example 2-ethoxy-1-ethoxycarbonyl-1,2-dihydroquinoline. Customary acid-binding condensation agents are, for example, alkali metal carbonates or hydrogen carbonates, for example sodium or potassium carbonate or hydrogen carbonate (customarily together with a sulfate), or organic bases, such as, customarily, pyridine or sterically hindered tri-lower alkylamines, for example N,N-diisopropyl-N-ethyl-amine.

In a preferred variant of process ii) a compound of formula V is reacted with a compound of formula VI in a suitable solvent, such as e.g. N,N-dimethylformamide, in the presence of propylphosphonic anhydride (Fluka, Buchs, Switzerland) and triethylamine, preferably at room temperature.

Process iii):

A suitable oxidising agent for converting a compound of formula I wherein $R_1$ is pyridyl into the N-oxido compound is preferably a suitable peracid, for example a suitable perbenzoic acid, such as especially m-chloro-perbenzoic acid. The reaction is carried out in an inert solvent, for example a halogenated hydrocarbon, such as preferably methylene chloride, at temperatures of approximately from −20° C. to +150° C., especially approximately from 0° C. to the boiling point of the solvent in question, in general below +100° C., and preferably at room temperature or at slightly elevated temperature (20° C.-70° C.).

Process iv):

Halogen in unsubstituted or optionally substituted halogen-lower alkyl-phenyl $R_{23}$ is preferably chloro.

The reaction is carried out in a manner known per se, for example by dissolving the reactants in a suitable solvent, for example ethanol, and boiling under reflux for from 10 to 20 hours.

The starting material of formula VIII is obtained by reacting a compound of formula XII

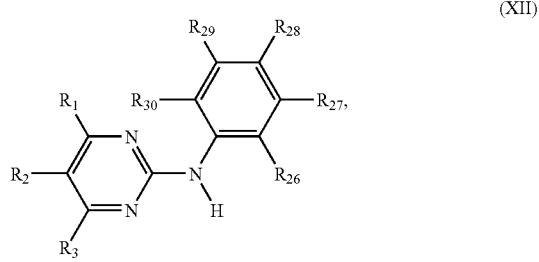

(XII)

wherein $R_1$, $R_2$ and $R_3$ are as defined above and one of the radicals $R_{26}$, $R_{27}$, $R_{28}$, $R_{29}$ and $R_{30}$ is a radical of the formula —N($R_9$)—H, wherein $R_9$ is as defined above, and the remaining radicals $R_{26}$, $R_{27}$, $R_{28}$, $R_{29}$ and $R_{30}$ are each independently of the others hydrogen; lower alkyl that is unsubstituted or substituted by free or alkylated amino, piperazinyl, piperidyl, pyrrolidinyl or by morpholinyl; lower alkanoyl; trifluoromethyl; free, etherified or esterified hydroxy; free, alkylated or acylated amino; or free or esterified carboxy, is reacted with a compound of formula XIII $$\text{Hal—C(=X)—(Y)}_n\text{—R}_{23} \qquad \text{(XIII),}$$

wherein Hal is halogen, preferably chloro, and the remaining substituents are as defined above.

The synthesis of a compound of formula XII is described in EP 0 564 409.

Acid addition salts of compounds of formula I are obtained in customary manner, for example by treatment with an acid or a suitable anion exchange reagent.

Acid addition salts can be converted into the free compounds in customary manner, for example by treatment with a suitable basic agent.

Mixtures of isomers can be separated into the individual isomers in a manner known per se, for example by fractional crystallization, chromatography, etc.

The processes described above, including the processes for removing protecting groups and the additional process steps, are, unless otherwise indicated, carried out in a manner known per se, for example in the presence or absence of preferably inert solvents and diluents, if necessary in the presence of condensation agents or catalysts, at reduced or elevated temperature, for example in a temperature range of from approximately −20° C. to approximately 150° C., especially from approximately 0° C. to approximately +70° C., preferably from approximately +10° C. to approximately +50° C., and more especially at room temperature, in a suitable vessel and if necessary in an inert gas atmosphere, for example a nitrogen atmosphere.

In those process steps, taking account of all the substituents in the molecule, if necessary, for example when readily hydrolysable radicals are present, especially mild reaction conditions should be used, such as short reaction times, the use of mild acidic or basic agents at low concentrations, stoichiometric quantity ratios, and the selection of suitable catalysts, solvents, temperature and/or pressure conditions.

The invention relates also to those forms of the process in which a compound obtainable as intermediate at any stage of the process is used as starting material and the remaining steps are carried out or the process is interrupted at any stage or a starting material is formed under the reaction conditions or is used in the form of a reactive derivative or salt. It is preferable to begin with those starting materials which in accordance with the process result in the compounds described above as being especially valuable.

Preferably the compounds of formula I are prepared according to the processes and process steps defined in the Examples.

The present invention relates also to novel starting materials and/or intermediates and to processes for the preparation thereof. The starting materials used and the reaction conditions chosen are preferably those which result in the compounds described in this Application as being especially preferred.

The invention relates also to a process for the treatment of warm-blooded animals, including humans, suffering from said diseases, especially a tumour disease, wherein a quantity of a compound of formula I which is effective against the disease concerned, especially a quantity with antiproliferative and especially tumour-inhibiting efficacy, is administered to warm-blooded animals, including humans, in need of such treatment. The invention relates moreover to the use of a compound of formula I for the inhibition of the above-mentioned tyrosine kinases, especially PDGF receptor kinase, v-abl kinase, and/or c-kit receptor kinase, or for the preparation of pharmaceutical compositions for use in treating the human or animal body, especially for the treatment of tumours, such as gliomas, ovarian tumours, prostate tumours, colon tumours, and tumours of the lung, such as especially small cell lung carcinoma, and tumours of the breast or other gynaecological tumours. Depending on species, age, individual condition, mode of administration, and the clinical picture in question, effective doses, for example daily doses of about 1-2500 mg, preferably 1-1000 mg, especially 5-500 mg, are administered to warm-blooded animals, including humans, of about 70 kg bodyweight.

The invention relates also to pharmaceutical preparations which contain an effective amount, especially an effective amount for prevention or treatment of one of the said diseases, of a compound of formula I together with pharmaceutically acceptable carriers which are suitable for topical, enteral, for example oral or rectal, or parenteral administration and may be inorganic or organic and solid or liquid. Especially tablets or gelatin capsules containing the active substance together with diluents, for example lactose, dextrose, sucrose, mannitol, sorbitol, cellulose, and/or glycerin, and/or lubricants, for example silica, talc, stearic acid, or salts thereof, typically magnesium or calcium stearate, and/or polyethylene glycol, are used for oral administration. Tablets may likewise contain binders, for example magnesium aluminium silicate, starches, typically corn, wheat or rice starch, gelatin, methylcellulose, sodium carboxymethylcellulose and/or polyvinylpyrrolidone, and, if so desired, disintegrants, for example starches, agar, alginic acid, or a salt thereof, typically sodium alginate, and/or effervescent mixtures, or adsorbents, colouring agents, flavours, and sweetening agents. The pharmacologically active compounds of the present invention may further be used in the form of preparations for parenteral administration or infusion solutions. Such solutions are preferably isotonic aqueous solutions or suspensions, these possibly being prepared before use, for example in the case of lyophilised preparations containing the active substance either alone or together with a carrier, for example mannitol. The pharmaceutical substances may be sterilised and/or may contain excipients, for example preservatives, stabilisers, wetting agents and/or emulsifiers, solubilisers, salts for the regulation of osmotic pressure, and/or buffers. The present pharmaceutical preparations which, if so desired, may contain further pharmacologically active substances, such as antibiotics, are prepared in a manner known per se, for example by means of conventional mixing, granulating, coating, dissolving or lyophilising processes, and contain from about 1% to 100%, especially from about 1% to about 20%, of the active substance or substances.

The following Examples illustrate the invention but do not limit the invention in any way. The $R_f$ values are determined on silica gel thin-layer plates (Merck, Darmstadt, Germany). The ratio to one another of the eluants in the eluant mixtures used is given in proportions by volume (v/v), and temperatures are given in degrees Celsius.

Abbreviations:
conc. concentrated
Ex. No. example number
min minute(s)
m.p. melting point
$t_R$ retention time
% w/w percent by weight

EXAMPLE 1

A suspension of 466 mg (1 mmol) of 4-chloromethyl-N-[4-methyl-3-(4-pyridin-3-yl-pyrimidin-2-ylamino)-phenyl]-benzamide hydrochloride in 25 ml of dry ethanol is treated with 381 μl (3 mmol) N-ethylpiperazine and then heated under reflux for 16 hours. The yellow solution is cooled to room temperature and decanted from a small amount of a brown insoluble residue which forms on the wall of the flask. The solvent is evaporated and the residue taken up in citric acid solution (10% w/w) and washed with dichloromethane. The aqueous layer is made basic by addition of sodium bicarbonate and sodium carbonate solution and extracted three times with 150 ml of dichloromethane containing 2 ml of ethanol. The combined organic extracts are washed with conc. sodium chloride solution, dried over sodium sulfate, and evaporated. The residue was stirred with 3 ml of ethyl acetate and the crystalline product filtered and washed with a small amount of ethyl acetate to obtain 4-(4-ethyl-piperazin-1-ylmethyl)-N-[4-methyl-3-(4-pyridin-3-yl-pyrimidin-2-ylamino)-phenyl]-benzamide; m.p. 209.5-210.5° C.; $t_R$ (HPLC)[1] 6.62 min.

EXAMPLES 2-8

Compounds are synthesized analogously to Example 1:

| Ex. No. | Compound | m.p. [° C.] | HPLC[1] $t_R$[min] |
|---|---|---|---|
| 2 | 4-Diethylaminomethyl-N-[4-methyl-3-(4-pyridin-3-yl-pyrimidin-2-ylamino)-phenyl]-benzamide | 148-151 | 7.23 |
| 3 | 4-Dimethylaminomethyl-N-[4-methyl-3-(4-pyridin-3-yl-pyrimidin-2-ylamino)-phenyl]-benzamide | 127-131 | 6.84 |
| 4 | N-[4-Methyl-3-(4-pyridin-3-yl-pyrimidin-2-ylamino)-phenyl]-4-pyrrolidin-1-ylmethyl-benzamide | 166-170 | 7.09 |
| 5 | N-[4-Methyl-3-(4-pyridin-3-yl-pyrimidin-2-ylamino)-phenyl]-4-morpholin-4-ylmethyl-benzamide | 219-221 | 6.84 |
| 6 | 4-(cis-3,5-Dimethyl-piperazin-1-ylmethyl)-N-[4-methyl-3-(4-pyridin-3-yl-pyrimidin-2-ylamino)-phenyl]-benzamide | 135.5-138.5 | 6.50 |
| 7 | N-[4-Methyl-3-(4-pyridin-3-yl-pyrimidin-2-ylamino)-phenyl]-4-piperidin-1-ylmethyl-benzamide | 197-199 | 6.66 |
| 8 | N-[4-Methyl-3-(4-pyridin-3-yl-pyrimidin-2-ylamino)-phenyl]-4-(4-propyl-piperazin-1-ylmethyl)-benzamide | 209-210 | 7.43 |

EXAMPLE 9

25.8 g (300 mmol) of piperazine are suspended in a mixture of 25 ml of ethanol and 25 ml of water. After almost a clear solution has formed, 12.9 g (30 mmol) of 4-chloromethyl-N-[4-methyl-3-(4-pyridin-3-yl-pyrimidin-2-ylamino)-phenyl]-benzamide are added step by step. The yellow solution is boiled under reflux for 14 hours, cooled to room temperature and filtered over Celite. 100 ml of water is added to the solution, the ethanol is evaporated under vacuum and 30 ml of 1N NaOH is added, leading to crystallization of the product. Drying at 50 mbar and 60° C. yields N-[4-methyl-3-(4-pyridin-3-yl-pyrimidin-2-ylamino)-phenyl]-4-piperazin-1-ylmethyl-benzamide;

$R_f$=0.15 (methylene chloride:ethyl acetate:methanol:conc. aqueous ammonium hydroxide solution=60:10:30:2); $t_R$ (HPLC)[2)] 14.6 min.

EXAMPLE 10

4.8 g (10 mmol) of N-[4-methyl-3-(4-pyridin-3-yl-pyrimidin-2-ylamino)-phenyl]-4-piperazin-1-ylmethyl-benzamide are dissolved in 20 ml of ethanol under heating and 0.99 g of methanesulfonic acid are added. After addition of ethyl acetate the product cristallizes. Drying at 50 mbar and 60° C. yields N-[4-methyl-3-(4-pyridin-3-yl-pyrimidin-2-ylamino)-phenyl]-4-piperazin-1-ylmethyl-benzamide methanesulfonate; $R_f$=0.17 (methylene chloride:ethyl acetate:methanol:conc. aqueous ammonium hydroxide solution=60: 10:30:2); $t_R$ (HPLC)[2)] 14.6 min; m.p. 242-245° C.

EXAMPLE 11

A solution containing approximately 50% of propylphosphonic anhydride in N,N-dimethylformamide (Fluka, Buchs, Switzerland; 700 μL, ~1.2 mmol) is added in portions within 20 min to a stirred mixture of 4-methyl-N-3-[4-(3-pyridinyl)-2-pyrimidinyl]-1,3-benzenediamine (221.9 mg, 0.8 mmol), 3-(dimethylamino)benzoic acid (Aldrich, Buchs, Switzerland; 132.2 mg, 0.8 mmol) and triethylamine (887 μL, 6.4 mmol) in 2 mL of dry N,N-dimethylformamide. After stirring for 48 hours at room temperature, the solvent is evaporated off under reduced pressure and the residue distributed between saturated aqueous sodium hydrogen carbonate solution and ethyl acetate. The aqueous phase is extracted twice with ethyl acetate. The combined extracts are dried ($Na_2SO_4$), filtered and the solvent is evaporated off under reduced pressure. The crude product is recrystallized from ethyl acetate/hexane to yield 3-dimethylamino-N-[4-methyl-3-[[4-(3-pyridinyl)-2-pyrimidinyl]amino]phenyl]-benzamide as a beige crystalline solid.

$^1$H-NMR (300 MHz, DMSO-$d_6$, δ): 2.18 (s, 3H); 2.92 (s, 6H); 6.87 (m, 1H); 7.12-7.51 (m, 7H); 8.03 (s, 1H); 8.39-8.50 (m, 2H); 8.64 (d, 1H); 8.95 (s, 1H); 9.24 (s, 1H); 10.05(s, 1H).

EXAMPLE 12

A solution containing approximately 50% of propylphosphonic anhydride in N,N-dimethylformamide (Fluka, Buchs, Switzerland; 700 μL, ~1.2 mmol) is added in portions within 20 min to a stirred mixture of 4-methyl-N-3-[4-(3-pyridinyl)-2-pyrimidinyl]-1,3-benzenediamine (221.9 mg, 0.8 mmol), 4-(dimethylamino)benzoic acid (Aldrich, Buchs, Switzerland; 132.2 mg, 0.8 mmol) and triethylamine (887 μL, 6.4 mmol) in 2 mL of dry N,N-dimethylformamide. After stirring for 48 h at room temperature, the solvent is evaporated off under reduced pressure and the residue distributed between saturated aqueous sodium hydrogen carbonate solution and ethyl acetate. The aqueous phase is extracted twice with ethyl acetate. The combined extracts are dried ($Na_2SO_4$), filtered and the solvent is evaporated off under reduced pressure to yield the crude product which is purified by column chromatography on silica gel, eluent 1-4% methanol in dichloromethane. The fractions containing the pure product are combined and the solvent is evaporated off. Crystallization of the residue from acetone gives 4-dimethylamino-N-[4-methyl-3-[[4-(3-pyridinyl)-2-pyrimidinyl]amino]phenyl]-benzamide as a yellow crystalline solid.

$^1$H-NMR (400 MHz, DMSO-$d_6$, δ): 2.19 (s, 3H); 2.97 (s, 6H); 6.73 (m, 2H); 7.14 (d, 1H); 7.39 (d, 1H); 7.42-7.52 (m, 2H); 7.83 (m, 2H); 8.02 (d, 1H); 8.41-8.49 (m, 2H); 8.65 (dd, 1H); 8.93 (s, 1H); 9.24 (m, 1H); 9.79 (s, 1H).

The following compounds are prepared analogously by utilising the appropriate acids:

EXAMPLE 13

4-(Acetylamino)-N-[4-methyl-3-[[4-(3-pyridinyl)-2-pyrimidinyl]amino]phenyl]benzamide utilising 4-acetamidobenzoic acid (Fluka, Buchs, Switzerland). $^1$H-NMR (400 MHz, DMSO-$d_6$, δ): 2.06 (s, 3H); 2.20 (s, 3H); 7.18 (d, 1H); 7.41 (d, 1H); 7.45 (dd, 1H); 7.50 (ddd, 1H); 7.69 (m, 2H); 7.90 (m, 2H); 8.04 (d, 1H); 8.46 (m, 1H); 8.49 (d, 1H); 8.66 (dd, 1H); 8.96 (s, 1H); 9.25 (dd, 1H); 10.05 (s, 1H); 10.20 (s, 1H).

EXAMPLE 14

3-(Acetylamino)-N-[4-methyl-3-[[4-(3-pyridinyl)-2-pyrimidinyl]amino]phenyl]benzamide utilising 3-acetamidobenzoic acid (Fluka, Buchs, Switzerland). $^1$H-NMR (400 MHz, DMSO-$d_6$, δ): 2.05 (s, 3H); 2.20 (s, 3H); 7.19 (d, 1H); 7.39-7.47 (m, 3H); 7.50 (ddd, 1H); 7.57-7.61 (m, 1H); 7.78-7.83 (m, 1H); 8.04-8.06 (m, 2H); 8.46 (m, 1H); 8.49 (d, 1H); 8.66 (dd, 1H); 8.97 (s, 1H); 9.25 (dd, 1H); 10.15 (s, 1H); 10.21 (s, 1H).

EXAMPLE 15

3-Hydroxy-4-methyl-N-[4-methyl-3-[[4-(3-pyridinyl)-2-pyrimidinyl]amino]phenyl]-benzamide utilising 3-hydroxy-4-methylbenzoic acid (Fluka, Buchs, Switzerland). $^1$H-NMR (400 MHz, DMSO-$d_6$, δ): 2.16 (s, 3H); 2.20 (s, 3H); 7.17 (m, 2H); 7.30-7.34 (m, 2H); 7.41 (d, 1H); 7.45 (dd, 1H); 7.50 (m, 1H); 8.05 (m, 1H); 8.46 (m, 1H); 8.49 (d, 1H); 8.66 (dd, 1H); 8.96 (s, 1H); 9.26 (m, 1H); 9.63 (s, 1H); 10.04 (s, 1H).

EXAMPLE 16

4-(1,1-Dimethylethyl)-N-[4-methyl-3-[[4-(3-pyridinyl)-2-pyrimidinyl]amino]phenyl]-benzamide utilising 4-tert-butylbenzoic acid (Fluka, Buchs, Switzerland). $^1$H-NMR (300 MHz, DMSO-$d_6$, δ): 1.30 (s, 9H); 2.20 (s, 3H); 7.18 (d, 1H); 7.40 (d, 1H); 7.42-7.54 (m, 4H); 7.85 (m, 2H); 8.04 (d, 1H); 8.42-8.50 (m, 2H); 8.66 (dd, 1H); 8.95 (s, 1H); 9.24 (m, 1H); 10.10 (s, 1H).

Analytical HPLC Conditions:

1) HPLC-System: Kontron 420 System; column: CC 250/4,6 nucleosil 100-5 C18; flow rate: 1 ml/min.

Eluents: A: water (+0.1% trifluoroacetic acid)
B: acetonitrile (+0.1% trifluoroacetic acid)

Gradient: 20%→0% A in B in 13 min and 100% B during 5 min.

2) HPLC-System: Column: 150×3.9 mm, packed with Symmetry C18 5μ (Waters), pre-equilibrated with eluent a); flow rate 1.2 ml/min, UV detection at 267 nm.

Eluents: a): ion pair reagent and methanol (420 ml+580 ml)
b): ion pair reagent and methanol (40 ml+960 ml)

Ion pair reagent: 7.5 g of 1-octanesulfonic acid dissolved in about 800 ml $H_2O$, pH value adjusted to 2.5 with phosphoric acid and diluted with water to 1000 ml Gradient: 0% b) in a) for 20 min, followed by 0%<30% b) in a) in 10 min and 30% b) in a) during 5 min.

EXAMPLE 17

Tablets containing 100 mg of a compound of formula I, for example one of the compounds of formula I described in the Examples 1-10, are usually prepared in the following composition:

| Composition: | |
|---|---|
| Active ingredient | 100 mg |
| Crystalline lactose | 240 mg |
| Avicel | 80 mg |
| PVPPXL | 20 mg |
| Aerosil | 2 mg |
| Magnesium stearate | 5 mg |
| | 447 mg |

Preparation: The active substance is mixed with carrier materials and compressed on a tableting machine (Korsch EKO, punch diameter 10 mm).
Avicel is microcrystalline cellulose (FMC, Philadelphia, USA).
PVPPXL is polyvinylpolypyrrolidone, cross-linked (BASF, Germany).
Aerosil is silicon dioxide (Degussa, Germany).

EXAMPLE 18

Capsules containing 100 mg of a compound of formula I, for example one of the compounds of formula I described in the Examples 1-10, are usually prepared in the following composition:

| Composition: | |
|---|---|
| Active ingredient | 100 mg |
| Avicel | 200 mg |
| PVPPXL | 15 mg |
| Aerosil | 2 mg |
| Magnesium stearate | 1.5 mg |
| | 318.5 mg |

Preparation: The capsules are prepared by mixing the components and filling the mixture into hard gelatin capsules, size 1.

What is claimed is:

1. A pharmaceutical composition comprising a therapeutically effective amount of a compound of formula I

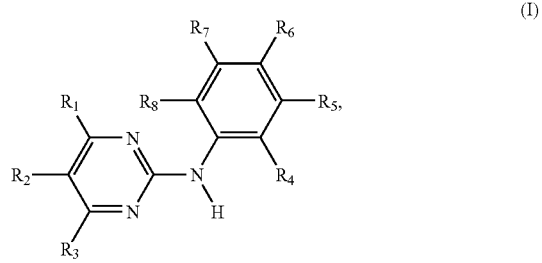

wherein
$R_1$ is pyridyl bonded at a ring carbon atom,
$R_2$ and $R_3$ are both hydrogen,
$R_4$ is lower alkyl,
$R_5$ and $R_6$ are both hydrogen,
$R_7$ is a radical of formula II —N($R_9$)—C(=X)—(Y)$_n$—$R_{10}$, wherein
$R_9$ is hydrogen,
x is oxo,
y is oxygen or the group NH,
n is 0 and
$R_{10}$ is phenyl which is substituted by piperazinyl-lower alkyl, and $R_8$ is hydrogen,
or a salt of such a compound having at least one salt-forming group together with a pharmaceutically acceptable carrier.

2. A pharmaceutical composition according to claim 1, wherein the compound of formula I is N-[4-methyl-3-(4-pyridin-3-yl-pyrimidin-2-ylamino)-phenyl]-4-piperazin-1-ylmethyl-benzamide methanesulfonate.

* * * * *